United States Patent
Hannigan et al.

(10) Patent No.: US 12,009,060 B2
(45) Date of Patent: Jun. 11, 2024

(54) IDENTIFYING BIOSYNTHETIC GENE CLUSTERS

(71) Applicants: Merck Sharp & Dohme LLC, Rahway, NJ (US); MSD Czech Republic s.r.o., Prague (CZ)

(72) Inventors: Geoffrey D. Hannigan, Melrose, MA (US); David Prihoda, Czech Republic (CZ); Jindrich Soukup, Prague (CZ); Christopher Harron Woelk, Winchester, MA (US); Danny A. Bitton, Czech Republic (CZ)

(73) Assignees: Merck Sharp & Dohme LLC, Rahway, NJ (US); MSD Czech Republic s.r.o., Smichov (CZ)

( * ) Notice: Subject to any disclaimer, the term of this patent is extended or adjusted under 35 U.S.C. 154(b) by 1452 days.

(21) Appl. No.: 16/362,236

(22) Filed: Mar. 22, 2019

(65) Prior Publication Data
US 2020/0194098 A1  Jun. 18, 2020

Related U.S. Application Data

(60) Provisional application No. 62/779,697, filed on Dec. 14, 2018.

(51) Int. Cl.
*G16B 30/00* (2019.01)
*G06N 3/044* (2023.01)
*G06N 3/045* (2023.01)

(52) U.S. Cl.
CPC ............ *G16B 30/00* (2019.02); *G06N 3/044* (2023.01); *G06N 3/045* (2023.01)

(58) Field of Classification Search
CPC ...... G16B 30/00; G16B 40/20; G06N 3/0445; G06N 3/0454; G06N 3/0481; G06N 3/08
See application file for complete search history.

(56) References Cited

U.S. PATENT DOCUMENTS

| 2018/0314704 A1* | 11/2018 | Bull | G06F 16/3329 |
| 2020/0012838 A1* | 1/2020 | Sharma | G06K 9/6273 |

OTHER PUBLICATIONS

Lyu, Chen, et al. "Long short-term memory RNN for biomedical named entity recognition." BMC bioinformatics 18.1 (2017): 1-11. (Year: 2017).*

(Continued)

*Primary Examiner* — Viker A Lamardo
*Assistant Examiner* — Sidney Vincent Bostwick
(74) *Attorney, Agent, or Firm* — Fenwick & West LLP (57) ABSTRACT

A BGC prediction system identifies candidate biosynthetic gene clusters (BGCs) within genomes using machine-learned models, such as a shallow neural network and recurrent neural network (RNN). A set of domains within a genome sequence are identified, each domain corresponds to a set of domain identifiers. A shallow neural network block is applied to each set of domain identifiers to produce a set of vectors. An RNN block is applied to the set of vectors to produce a BGC class score for each domain. The RNN block was trained using an identified set of positive vectors, which represents known BGCs, and a synthesized set of negative vectors, which is unlikely to represent BGCs. Candidate BGCs are selected by averaging BGC class scores across genes within a domain and comparing the average BGC class scores to a threshold. The candidate BGCs are provided for display on a user interface.

20 Claims, 5 Drawing Sheets

(56) References Cited

OTHER PUBLICATIONS

Purcell, Shaun, et al. "PLINK: a tool set for whole-genome association and population-based linkage analyses." The American journal of human genetics 81.3 (2007): 559-575. (Year: 2007).*
Brito, Thais L., et al. "The gill-associated microbiome is the main source of wood plant polysaccharide hydrolases and secondary metabolite gene clusters in the mangrove shipworm Neoteredo reynei." PLoS One 13.11 (2018): e0200437. (Year: 2018).*
Abu-Jamous, Basel, and Steven Kelly. "Clust: automatic extraction of optimal co-expressed gene clusters from gene expression data." Genome biology 19.1 (2018): 1-11. (Year: 2018).*
Collobert, Ronan, et al. "Natural language processing (almost) from scratch." Journal of machine learning research 12.Article (2011): 2493-2537. (Year: 2011).*
Xu, Zheng, et al. "Seq2seq fingerprint: An unsupervised deep molecular embedding for drug discovery." Proceedings of the 8th ACM international conference on bioinformatics, computational biology, and health informatics. 2017. (Year: 2017).*
Rajkumar, et al. "sequence-prediction-using-CNN-and-LSTMs", captured from https://github.com/rajkumar1501/sequence-prediction-using-CNN-and-LSTMs/tree/61e2da0acc4b65910267b9ca954936465c87004e on Aug. 19, 2022 (Year: 2018).*
Chakraborty, Rajkumar. MIRBOT: a Micrcorna Sequence Prediction Tool From Targeted RNA Sequence Segment Based on CNN and LSTMS Stacked in SEQ2SEQ Architecture. Diss. 2018. (Year: 2018).*
Altschul, S. F. et al., "Basic local alignment search tool," Journal of Molecular Biology, Oct. 5, 1990, pp. 403-410, vol. 215, No. 3.
Anantharaman, V. et al., "New connections in the prokaryotic toxin-antitoxin network: relationship with the eukaryotic nonsense-mediated RNA decay system," Genome Biology, 2003, 15 pages, vol. 4, No. 12.
Armstrong, R. N., "Mechanistic Diversity in a Metalloenzyme Superfamily," Biochemistry, Nov. 14, 2000, pp. 13625-13632, vol. 39, No. 45.
Asgari, E. et al., "Continuous Distributed Representation of Biological Sequences for Deep Proteomics and Genomics," PLoS One, Nov. 10, 2015, 15 pages, vol. 10.
Chavadi, S. S. et al., "Mutational and Phylogenetic Analyses of the Mycobacterial mbt Gene Cluster," Journal of Bacteriology, Nov. 2011, pp. 5905-5913, vol. 193, No. 21.
Choo, K. H. et al., "Recent Applications of Hidden Markov Models in Computational Biology," Genomics, Proteomics & Bioinformatics, May 2004, pp. 84-96, vol. 2, No. 2.
Cimermancic, P. et al., "Insights into Secondary Metabolism from a Global Analysis of Prokaryotic Biosynthetic Gene Clusters," Cell, Jul. 17, 2014, pp. 412-421, vol. 158, No. 2.
Decorte, B. L., "Underexplored Opportunities for Natural Products in Drug Discovery," Journal of Medicinal Chemistry, 2016, pp. 9295-9304, vol. 59.
Eddy, S. R., "Profile hidden Markov models," Bioinformatics, 1998, pp. 755-763, vol. 14, No. 9.
Eddy, S. R., "What is a hidden Markov model," Nature Biotechnology, 2004, pp. 1315-1316, vol. 22.
Finn, R. D. et al., "The Pfam protein families database: towards a more sustainable future," Nucleic Acids Research, Jan. 4, 2016, pp. D279-D285, vol. 44, No. D1.
Hannigan, G. D. et al., "A deep learning genome-mining strategy for biosynthetic gene cluster prediction," Nucleic Acids Research, Oct. 10, 2019, 13 pages, vol. 47, No. 18.
Harris, N. C. et al., "Biosynthesis of isonitrile lipopeptides by conserved nonribosomal peptide synthetase gene clusters in Actinobacteria," Proceedings of the National Academy of Sciences of the United States of America, Jul. 3, 2017, pp. 7025-7030, vol. 114, No. 27.
Harvey, A. L. et al., "The re-emergence of natural products for drug discovery in the genomics era," Nature Reviews Drug Discovery, Feb. 2015, pp. 111-129, vol. 14, No. 2.

Hochreiter, S. et al., "Fast model-based protein homology detection without alignment," Bioinformatics, Jul. 15, 2007, pp. 1728-1736, vol. 23, No. 14.
Hochreiter, S. et al., "Long Short-Term Memory," Neural Computation, Nov. 15, 1997, pp. 1735-1780, vol. 9, No. 8.
Hopwood, D. A. et al., "Genetics of Antibiotic Production," Bacteriology Reviews, Sep. 1977, pp. 595-635, vol. 41., No. 3.
Hyatt, D. et al., "Prodigal: prokaryotic gene recognition and translation initiation site identification," BMC Bioinformatics, 2010, 11 pages, vol. 11.
Kim, S. et al., "Mut2Vec: distributed representation of cancerous mutations," BMC Medical Genomics, Apr. 20, 2018, pp. 57-69, vol. 11, No. 2.
Lecun, Y. et al., "Deep learning," Nature, May 28, 2015, pp. 436-444, vol. 521.
Li, W. et al., "Comparative Genomic Insights Into the Biosynthesis and Regulation of Myobacterial Siderophores," Cellular Physiology and Biochemistry, 2013, 13 pages, vol. 31.
Martin, J. F. et al., "Organization and Expression of Genes Involved in the Biosynthesis of Antiobiotics and Other Secondary Metabolites," Annual Review of Microbiology, 1989, 36 pages, vol. 43.
Martin, J. F., "Clusters of genes for the biosynthesis of antibiotics: regulatory genes and overproduction of pharmaceuticals," Journal of Industrial Microbiology, 1992, pp. 73-90, vol. 9., No. 2.
Medema, M. H. et al., "antiSMASH: rapid identification, annotation and analysis of secondary metabolite biosynthesis gene clusters in bacterial and fungal genome sequences," Nucleic Acids Research, Jul. 1, 2011, pp. W339-W346, vol. 39.
Medema, M. H. et al., "Computational approaches to natural product discovery," Nature Chemical Biology, Sep. 2015, pp. 639-648, vol. 11.
Medema, M. H. et al., "Minimum Information about a Biosynthetic Gene cluster," Nature Chemical Biology, Sep. 2015, pp. 625-631, vol. 11, No. 9.
Mikolov, T. et al., "Efficient Estimation of Word Representations in Vector Space," arXiv preprint arXiv:1301.3781, Sep. 7, 2013, 12 pages.
Milshteyn, A. et al., "Mining the Metabiome: Identifying Novel Natural Products from Microbial Communities," Chemistry & Biology, Sep. 18, 2014, pp. 1211-1223, vol. 21, No. 9.
Newman, D. J. et al., "Natural Products As Sources of New Drugs over the 30 Years from 1981 to 2010," Journal of Natural Products, Mar. 2012, 32 pages, vol. 75, No. 3.
O'Leary, N. A. et al., "Reference sequence (RefSeq) database at NCBI: current status, taxonomic expansion, and functional annotation," Nucleic Acids Research, Jan. 4, 2016, pp. D733-D745, vol. 44, No. D1.
Pendleton, J. N. et al., "Clinical relevance of the ESKAPE pathogens," Expert Reviews, 2013, pp. 297-308, vol. 11, No. 3.
Quadri, L. E. N. et al., "Identification of Myobacterium tuberculosis gene cluster encoding the biosynthetic enzymes for assembly of the virulence-conferring siderophore myobactin," Chemistry & Biology, Nov. 1998, pp. 631-645, vol. 5, No. 11.
Schuster, M. et al., "Bidirectional Recurrent Neural Networks," IEEE Transactions on Signal Processing, Nov. 1997, pp. 2673-2681, vol. 45, No. 11.
Shen, B., "A New Golden Age of Natural Products Drug Discovery," Cell, Dec. 3, 2015, pp. 1297-1300, vol. 163, No. 6.
Skinnider, M. A. et al., "PRISM 3: expanded prediction of natural product chemical structures from microbial genomes," Nucleic Acids Research, Jul. 3, 2017, pp. W49-W54, vol. 45, No. W1.
Tobias, N. J. et al., "Complete Genome Sequence of the Frog Pathogen Myobacterium ulcerans Ecovar Liflandii," Journal of Bacteriology, Feb. 2013, pp. 556-564, vol. 195, No. 3.
Ventola, C. L. et al., "The Antibiotic Resistance Crisis, Part 1: Causes and Threats," P&T, Apr. 2015, pp. 277-283, vol. 40, No. 4.
Weber, T. et al., "CLUSEAN: A computer-based framework for the automated analysis of bacterial secondary metabolite biosynthetic gene clusters," Journal of Biotechnology, 2009, pp. 13-17, vol. 140.
Yoon, B. J., "Hidden Markov Models and their Applications in Biological Sequence Analysis," Current Genomics, 2009, pp. 402-415, vol. 10, No. 6.

(56) References Cited

OTHER PUBLICATIONS

Zhang, H. et al., "Current status and future directions of cancer immunotherapy," Journal of Cancer, 2018, pp. 1773-1781, vol. 9., No. 10.

Ziemert, N. et al., "The evolution of genome mining in microbes—a review," Natural Product Reports, Aug. 2016, pp. 988-1005, vol. 33., No. 8.

* cited by examiner

IDENTIFYING BIOSYNTHETIC GENE CLUSTERS

CROSS-REFERENCE TO RELATED APPLICATION

This application claims benefit of U.S. Provisional Patent Application Ser. No. 62/779,697, filed Dec. 14, 2018, which is hereby incorporated by reference in its entirety.

TECHNICAL FIELD

The disclosure generally relates to the field of modeling, and in particular to identifying biosynthetic gene clusters within genomes.

BACKGROUND

Natural products are chemical compounds that are found in nature and produced by living organisms. They represent a rich reservoir of small molecule drug candidates that have marked a cornerstone in drug discovery. These small molecule natural products have been used in myriad applications including antibacterial and other antimicrobial drugs, anticancer drugs, antidiabetic drugs, hypocholesterolemic drugs, and immunomodulatory agents. However, the global rise in antibiotic resistance, increased promise of immunomodulatory agents in cancer treatment, and continued need for development of new drugs across applications incentivizes continuous identification of novel bioactive compounds.

Small molecule natural products may be produced by biosynthetic gene clusters (BGCs). A BGC is a group of genes located in close genomic proximity that encode the biosynthetic pathway for the production of secondary metabolites via a complex pathway of metabolic and regulatory switches.

Current methods of identifying BGCs rely on trial and error. Given the vast number of gene clusters present in nature, and the relative scarcity of BGCs, current methods require prohibitively large amounts of time and resources. As a result, current methods are limited in their ability to identify BGCs. Therefore, a new and improved method of BGC identification is needed.

SUMMARY

Embodiments relate to the identification of biosynthetic gene clusters (BGCs) within genomes. Machine-learned models, such as a shallow network and a recurrent neural network, identify candidate BGCs within domains of genome sequences. Users may be provided the newly identified candidate BGCs on a user interface.

In various embodiments, a method of identifying candidate BGCs within genomes includes identifying a set of domains within a genome sequence. Each domain in the genome sequence corresponds to a set of domain identifiers. The method also includes applying a shallow neural network block to each set of domain identifiers to produce a set of vectors. Each vector corresponds to a set of domain identifiers. The method further includes applying a recurrent neural network (RNN) block to the set of vectors to produce a BGC class for each domain. The RNN block was trained by identifying a set of positive vectors representing known BGCs. A set of negative vectors unlike to represent BGCs is synthesized. The RNN block is applied to the positive and negative sets of vectors to generate predictions of whether each vector is a positive or negative vector. The weights of the RNN block are updated based on the predictions. The method further includes selecting candidate BGCs by averaging BGC class scores across genes within a domain and comparing the average BGC class score to a threshold. The method further includes providing for display, on a user interface, the candidate BGCs.

The method of identifying candidate BGCs may further include processing candidate BGCs. Processing may include merging and filtering candidate BGCs based on the presence of known BGCs, a cluster length, or a distance between candidate BGCs. The method of identifying candidate BGCs may also include merging consecutive candidate BGC genes. The method of applying the RNN block to the set of vectors may also include applying a sigmoid activation function. The RNN block may be a bi-directional long short-term memory (LSTM) block. The domain identifiers may be maintained in genomic order. Each vector in the set of vectors may comprise one hundred elements, where each element is a real number and represents a property of the domain based on its genomic order. A secondary metabolite class based on the biosynthetic product and molecular activity of each candidate BGC may be predicted using a classifier. For example, the classifier may be a random forest classifier.

The set of negative vectors may be synthesized by a process that includes retrieving a genome sequence with known BGCs. The process also includes modifying the genome sequence by replacing a portion of the genes within the known BGCs with random genes of similar length. The process also includes generating a set of identifiers for each domain in the modified genome sequence. The process also includes applying a shallow neural network block to each domain in the modified genome sequence to produce a set of negative vectors.

In other embodiments, a BGC identification system is stored on a machine-readable storage medium. The BGC identification system is manufactured by a process including identifying a set of domains in a genome sequence, each identified domain corresponding to a set of identifiers. The process further includes applying a shallow neural network block to each set of domain identifiers to produce a set of vectors. Each vector in the set of vectors corresponds to a set of domain identifiers. The process further includes applying an RNN block to the set of vectors to produce a BGC class score for each domain. The RNN block was trained by identifying a set of positive vectors representing known BGCs, synthesizing a set of negative vectors unlikely to represent BGCs, applying the RNN block to the positive and negative vectors to generate predictions of whether each vector is a positive or negative vector, and updating the weights of the RNN block based on the predictions. Candidate BGCs are selected by averaging BGC class scores across genes within a domain and comparing the average BGC class scored to a threshold. The process further including providing the candidate BGCs for display on a user interface.

BRIEF DESCRIPTION OF THE DRAWINGS

The disclosed embodiments have advantages and features which will be more readily apparent from the detailed description, the appended claims, and the accompanying figures (or drawings). A brief introduction of the figures is below.

DETAILED DESCRIPTION

The Figures (FIGS.) and the following description relate to preferred embodiments by way of illustration only. It is noted that wherever practicable similar or like reference numbers may be used in the figures and may indicate similar or like functionality. One skilled in the art will readily recognize from the following description that alternative embodiments of the structures and methods illustrated herein may be employed without departing from the principles described herein.

Overview of Method

BGCs can be identified within bacterial genomes due to their enzymatic and topological properties. BGCs can be presented as a sequence of protein family (pfam) domains in which distinctive patterns may be located in the genome and new BCG candidates identified based on those patterns and known BCGs. Described herein is a method of identifying BGCs within genomes that can detect such dependencies, enabling informative signatures of BGC identification to be obtained. The method also preserves position dependency effects between distant genome entities and order information, enabling higher order information among genomic entities to be captured.

In various embodiments, a shallow neural network model is applied to each set of pfam domain identifiers to produce a vector for each pfam domain. The vectors are generated using natural language processing (NLP) techniques to represent each set of identifiers as a vector of real numbers. A second vector may also be generated for each set of identifiers identifying the location of each pfam domain within a protein. The two vectors may be concatenated into a single vector before a trained recurrent neural network (RNN) is applied to the set of vectors. The RNN may include a bi-directional long short-term memory (LSTM) model and a sigmoid activation function. In one embodiment, the output of the RNN is a single output unit for each pfam domain, e.g., a BGC classification score. In other embodiments, the RNN may output more than one output unit for each pfam domain.

In various embodiments, the BGC classification scores are summarized across genes to produce a single BGC classification score for each gene. To identify candidate BGCs, the summarized scores are compared to a threshold. If a summarized score is greater than a threshold, the BGC is identified as a candidate BGC. Biosynthetic product class and activity may also be predicted for candidate BGCs. The candidate BGC and predicted biosynthetic product class and activity are provided to a user for display.

The RNN is trained and validated using positive and negative training datasets. Positive and negative training sets are generated from genomes with labeled BGCs. Reference genomes with labeled BGCs are used as the positive set, while the negative set is produced by modifying reference genomes to remove the likelihood one will contain a BGC. To do this, all known BGCs are removed from a reference genome to produce a non-BGC sequence. Genes from the non-BGC sequence are randomly selected to replace genes from known BCGs in a different reference genome. This process is repeated to produce the negative training set. The positive and negative training sets are concatenated and shuffled to produce an artificial genome with realistic properties—regions of known BGCs surrounds by regions without BGCs. A shallow neural network is applied to the set of domain identifiers of each domain in the artificial genome to produce a set of numeric vectors. A RNN is applied to the set of numeric vectors to produce a BGC classification score for each domain in the artificial genome. The weights and parameters of the RNN are updated by comparing the expected output of the RNN to the realized output of the RNN block until a predetermined level of accuracy is achieved.

Example BGC Prediction System

Figure 1:
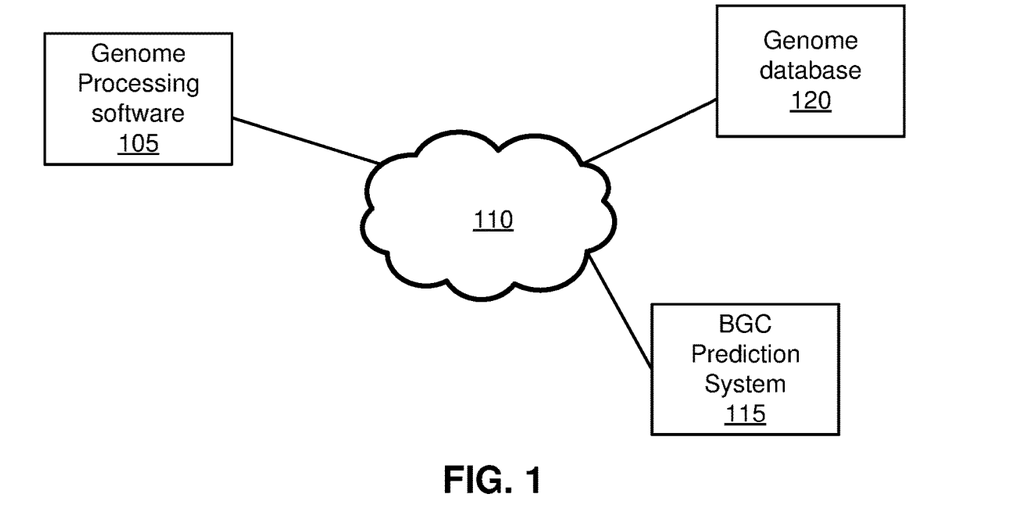
FIG. 1 illustrates a system environment for identifying biosynthetic gene clusters (BGCs), according to one embodiment.

Figure (FIG. 1 illustrates one embodiment of a system environment 100 for identifying biosynthetic gene clusters (BGCs). In the embodiment shown, the system environment 100 includes a genome processing software 105, a BGC prediction system 115, and a genome database 120 connected via a network 110. In other embodiments, the system environment 100 includes different and/or additional elements. In addition, the functions may be distributed among the elements in a different manner than described.

The genome processing software 105 is one or more software applications or programs that are used to process genome data. For example, the software programs may be used to sequence a genome, identify protein family domains, search protein sequences, or the like. In one embodiment, the software with similar or identical functionality is integrated into the BGC prediction system 115.

The BGC prediction system 115 identifies regions within genomes that are likely to contain BGCs. The BGC prediction system 115 represents genome data (e.g., sequenced genomes) as feature vectors and applies an artificial neural network to identify potential BGCs within the genome data. The BGC prediction system 115 may also classify the potential BGCs based on their biosynthetic product and molecular activity. Embodiments of the BGC prediction system 115 are described in greater detail below, with reference to FIG. 2.

The genome database 120 is one or more databases that store genomic information. For example, the databases may store genome sequences, location information of known BGCs, metadata, biosynthetic product classes and activity of known BGCs, and the like. In other embodiments, the genomic information is stored in a database integrated into the BGC prediction system 115.

The network 110 facilitates communication between the BGC prediction system 115, the genome processing software 105, and the genome database 120. The network 110 may be any wired or wireless local area network (LAN) and/or wide area network (WAN), such as an intranet, an extranet, or the Internet. In various embodiments, the network 110 uses standard communication technologies and/or protocols. Examples of technologies used by the network 110 include Ethernet, 802.11, 3G, 4G, 802.16, or any other suitable communication technology. The network 110 may use wireless, wired, or a combination of wireless and wired communication technologies. Examples of protocols used by the network 110 include transmission control protocol/Internet protocol (TCP/IP), hypertext transport protocol (HTTP), simple mail transfer protocol (SMTP), file transfer protocol (TCP), or any other suitable communication protocol. Data exchanged over the network 110 may be represented using any suitable format, such as hypertext markup language (HTML) or extensible markup language (XML). In some embodiments, all or some of the communication links of the network 110 may be encrypted using any suitable technique or techniques.

Figure 2:
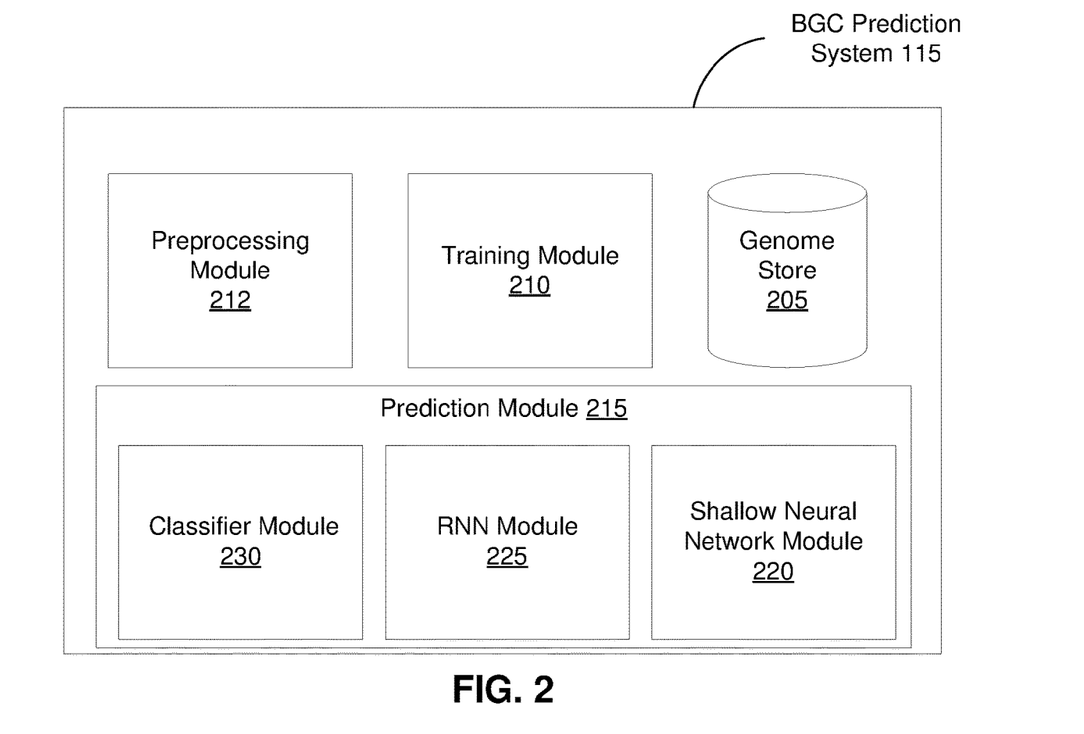
FIG. 2 is a block diagram of a BGC prediction system, according to one embodiment.

FIG. 2 shows one embodiment of the BGC prediction system 115 of FIG. 1. In the embodiment shown in FIG. 2, the BGC prediction system 115 includes a genome store 205, a training module 210, a preprocessing module 212, and a prediction module 215, which contains a classifier module 230, a RNN module 225, and a shallow neural network module 220. In other embodiments, the BGC prediction system 115 includes different and/or additional elements. In addition, the functions may be distributed among the elements in a different manner than described.

The BGC prediction system 115 maintains genome data in the genome store 205. Genome data may contain whole or portions of genomes and corresponding metadata. In one embodiment, the genome store 205 contains information about known BGCs within genomes, including their locations within the corresponding genome. This information can be obtained from a genome database 120 or obtained using a genome processing software 105. In addition, the genome store 205 may contain information about the biosynthetic products and functionality of known BGCs. The genome store 205 may additionally contain information about regions of genomes that are unlikely to or known to not contain BGCs.

The training module 210 trains models for use by the prediction module 215. In particular, the training module 210 may train a shallow neural network model contained in the shallow neural network module 220, a recurrent neural network model contained in the RNN module 225, and/or a classifier model contained in the classifier module 230. The shallow neural network module 220 generates real-number vectors representing genome data, the recurrent neural network module 225 identifies candidate BGCs, and the classifier module 230 predicts product classes and molecular activity for candidate BCGs.

To train and validate the models, the training module 210 adjusts the model parameters of each model using positive and negative training sets. The training module 210 can obtain training sets from the genome store 205 or a genome database 120. Additional training sets can also be generated by the training module 210, the preprocessing module 212, or a genome processing software 105. Positive training sets are labeled BGC genomes. Genomes containing identified BGCs are well documented in the scientific community and are readily available. The location and nature of identified BGC regions in genome data may be obtained from a genome database 120, using genome processing software 105, or from the genome store 205.

Negative training sets correspond to sequences that are highly unlikely to contain BGCs. It is more difficult, however, to affirmatively obtain non-BGC sequences. This is because while it is possible to determine where known BGCs are present, but it is difficult to state that a given sequence is not a BGC without testing that sequence, which is time consuming and defeats the object of predicting the location of unknown BGCs. To combat this difficulty, negative training sets may be generated by removing known BGCs from positive training sets and replacing them with random genes of similar length, discussed in detail below, with reference to FIG. 5. Positive and negative training sets are used to produce artificial genomes for model training and validation.

The preprocessing module 212 preprocesses genome data before it is fed into the prediction module 215. The preprocessing module 212 can predict genes and open reading frames (ORFs) within genome sequences obtained from the genome store 205 or from a genome database 120. In some embodiments, the prediction module 212 identifies domains (e.g., protein family (pfam) domains) within the genes and generates domain identifiers for each domain. In other embodiments, a genome processing software 105 may be used to obtain the location of domains within the genes and generate corresponding domain identifiers. The preprocessing module 212 directs the preprocessed genome data (i.e., preprocessed genome sequences) to the prediction module 215.

The prediction module 215 facilitates the identification and classification of BGCs within genomes. In one embodiment, the prediction module 215 contains three modules, namely, the shallow neural network module 220, the RNN module 225, and the classifier module 230. In other embodiments, different and/or additional modules may be contained in the prediction module 215. The prediction module 215 retrieves one or more genomes from the genome store 205 or genome database 120.

The prediction module 215 provides the unlabeled genomes, ORFs, domains, and domain identifiers to the shallow neural network module 220. In some embodiments, the prediction module 215 directs the output of the shallow neural network module 220 to the RNN module 225. Similarly, in some embodiments, the prediction module 215 directs the output of the RNN module 225 to the classifier module 230. In other embodiments, the prediction module 215 directs the output of each sub-module to the genome store 205.

The shallow neural network module 220 contains a shallow neural network to process genome data. The shallow neural network module 220 receives the genome data as an ordered list of domains from the preprocessing module 212. The shallow neural network processes the genome data using natural language processing (NLP) techniques to produce numeric vectors for domains in the sequence that encapsulate the properties of the domains based on their genome context. In some embodiments, the shallow neural network is a variation of a word2vec algorithm with skip-gram architecture termed "pfam2vec." In other embodiments, the shallow neural network is a word2vec algorithm with continuous bag-of-words architecture. The shallow neural network module 220 may also generate a second set of vectors for each genome sequence. Each vector in the second set of vectors contains one or more binary flags for each domain within a genome sequence.

The RNN module 225 contains a recurrent neural network (RNN) model to process the output of the shallow neural network module 220. In some embodiments, the RNN model is a LSTM model. In other embodiments, the RNN model is a bi-directional LSTM (BiLSTM) model, described in greater detail below, with reference to FIG. 4. The RNN module 225 also contains an activation function. In some embodiments, the activation function is a sigmoid activation function. In other embodiments, the activation function is a linear function, a ReLu function, a tanh functions, etc.

The RNN module 225 retrieves the output (as sets of vectors) of the shallow neural network module 220. Using the retrieved sets of vectors, the RNN module 225 produces a BGC classification score for each pfam domain, and identifies candidate BGCs using the classification scores, described in greater detail below, with reference to FIG. 4. The RNN module 225 may direct the classification scores and candidate BGCs to the classifier module 230 that classifies candidate BGCs based on their predicted biosynthetic product classes and activity. The RNN module 230 may also direct the BGC classification scores and candidate BGCs to the genome store 205.

The classifier module 230 predicts and stores secondary metabolite classes and/or molecular activity for candidate BGCs. The classifier module 230 retrieves the classification scores associated with each pfam domain from the RNN module 225 or the genome store 205. In one embodiment, the classifier module 230 contains one or more trained random forest classifiers. In other embodiments, different classifiers are used to predict the secondary metabolite classes and molecular activity of the candidate BGCs (e.g, support vector machines, neural network classifiers, bootstrap aggregated trees, etc.). The classifier module 230 may store the output of the classifiers in the genome store 205 (e.g., as metadata associated with the corresponding genome sequence).

Figure 3:
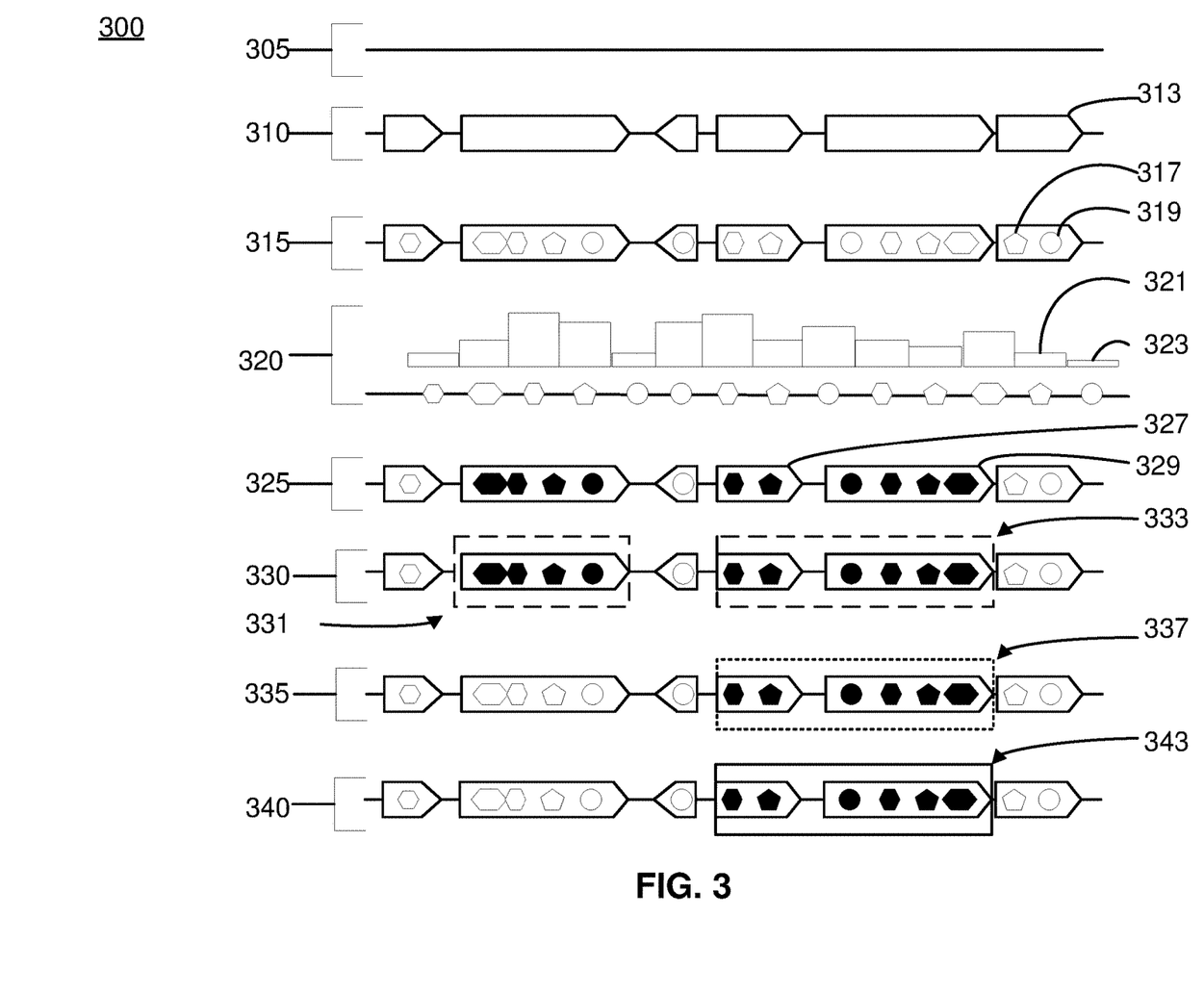
FIG. 3 illustrates an overview of a strategy for the identification of BGCs in genomes, according to one embodiment.

FIG. 3 illustrates an overview 300 of a strategy for the detection of BGCs in genome sequences, according to one embodiment. In some embodiments, one or more genome sequences are retrieved from the genome store 205 or a genome database 120. A genome sequence 305, represented as a blank line is used for gene prediction. In some embodiments, a genome sequence 305 corresponds to bacterial genomes. In other embodiments, genome sequences correspond to viral genomes, prokaryotic genomes, eukaryotic genomes, etc. In one embodiment, the sequence of an entire genome is retrieved. In other embodiments, a sequence corresponding to a portion (or portions) of a genome is retrieved.

Genes, represented as arrowhead structures, e.g., gene 313, are identified and highlighted 310 within the genome sequence. The locations of the genes within the genome sequence 305 are predicted using open reading frames (ORFs). ORFs are regions (reading frames) of genomes that have an ability to be translated to create a protein, which assists in gene prediction. An ORF is typically a continuous stretch of codons that begins with a start codon (e.g., AUG) and ends at a stop codon (e.g., UAA, UAG, or UGA). In some embodiments, ORFs are identified using a genome processing software. Examples of third party software applications include Prodigal Gene Prediction Software and ORF Finder. In other embodiments, genes are predicted using the preprocessing module 212 in the BGC prediction system 115 or information stored in the genome store 205. In other embodiments, the location of genes within the genome sequence 305 can be retrieved from information stored in a genome database 120.

Pfam domains (represented as polygons and circles) are assigned 315 to each gene. For example, gene 313 contains two pfam domains, e.g., pfam domain 317 and pfam domain 319. In one embodiment, pfam domains are assigned 315 to each gene using a genome processing software 105. Examples of genome processing software 105 include HMMER, HMMScan, and the like. In other embodiments, pfam domains are assigned 315 to each gene by the preprocessing module 212 or using information stored in a genome database 120 or the genome store 205. The resulting list of pfam domains are sorted by gene start location and the domain start location.

A set of pfam domain identifiers is identified for each pfam domain. The shallow neural network model is applied to each set of identifiers to produce a numeric vector for each domain. BGC classification scores are computed 320 for the pfam domains to represent the likelihood that the pfam domains are part of a BGC region. In various embodiments, BGC classification scores, represented as bars, e.g., 321 and 323, are computed 320 through the application of a model and activation function to each numeric vector associated with a pfam domain. For example, BGC classification score 321 corresponds to the BGC classification score of pfam domain 317, and BGC classification score 323 corresponds to the BGC classification score of pfam domain 319. The model may be a BiLSTM and the activation function may be a sigmoid activation function, described in detail with reference to FIG. 4. Alternatively, the model may be a convolutional neural network, another type of recursive neural network, etc., and the activation function may be a linear function, a ReLu function, a tanh function, etc.

BGC classification scores for each pfam domain are summarized 325 across genes. Genes with summarized BGC classification scores are represented as filled-in polygons and circles. For example, the pfam domains in genes 327 and 329 are summarized and represented by a single BGC classification score. Summarized BGC classification scores can also be represented as a range of scores, e.g., based on a median, average, standard deviation, upper and lower confidence limits. Summarized BGC classifications scores are used to identify candidate BGC genes.

Candidate BGCs, represented with medium dashed boxes, are identified 330 by comparing summarized BGC classification scores against a threshold. In some embodiments, users select a threshold based on a desired false-positive rate, e.g., a value between 0 and 1 that indicates the desired false-positive rate. In other embodiments, users select a threshold based on a desired true-positive rate, e.g. a value between 0 and 1 that indicates a desired true-positive rate. Genes with summarized BGC classification scores above the threshold may be identified 330 as candidate BGCs, e.g., gene 331. Consecutive candidate BGC genes are merged before classification into a single candidate BGC region. For example, gene 327 and gene 329 were merged into a single putative BGC 333.

In some embodiments, post-processing steps are applied 335 to candidate BGCs. Post-processing steps may include applying filters and merging candidate BGC genes into a single candidate BGC. In one embodiment, candidate BGCs are filtered out if they contain less than a threshold number of kilobases (Kb) (e.g., 1 Kb, 2 Kb, 10 Kb, etc.). In another embodiment, BGCs are filtered out if they do not contain any known biosynthetic domains. Examples of known biosynthetic domains are biosynthetic domains published by antiSMASH. In one embodiment, candidate BGCs are merged together if they are located consecutively or are at most one gene apart, e.g., candidate BGC 337 was produced when candidate BGC gene 327 and candidate BGC gene 329 were merged into a single candidate BGC. In other embodiments, consecutive candidate BGCs are merged into a single candidate BGC if they contain less than a threshold number of kilobases.

The biosynthetic products derived from predicted BGCs and their corresponding molecular activity BGC can be predicted 340 for the candidate BGCs, e.g., candidate BGC 343. To identify the biosynthetic product, candidate BGCs are assigned to compound classes using one or more trained random forest classifiers. Class assignment is based on the composition of the pfam domains within a candidate BGC and their underlying biosynthetic products. In some embodiments, candidate BGCs classes are predicted using a multilabel classification system, where each sample is labeled with a binary vector representing the presence of zero or more classes. In some embodiments, classes include Polyketide, NRP, RiPP, Saccharide, Terpene, and Alkaloid classes. In other embodiments, candidate BGCs can be classified into "novel" classes not yet identified by other genome processing software systems.

In some embodiments, candidate BGCs are also classified into classes of molecular activity based on their compound activity using the classifier module 230. Molecular activity may be determined using one or more trained random forest classifiers. In one embodiment, candidate BGCs are classified into four activity classes, namely, antibacterial, cytotoxic, inhibitor, and antifungal. In other embodiments, candidate BGCs can be classified into more, fewer, or different classes based on compound activity.

In various embodiments, classifiers are trained and tested using labeled BGCs belonging to one or more compound classes and/or one or more activity classes, including the classes discussed above. Biosynthetic product class and activity training data may be obtained from a genome database, e.g., the Minimum Information about a Biosynthetic Gene cluster (MIBiG) database. Product classes and product activities are extracted from the labelled training samples. A separate classifier may be trained for both problem domains using genome processing software, e.g., the scikit-learn python module (version 0.19.1), or software integrated into the BGC prediction system 115. Examples of classifiers may include random forest classifiers, support vector machines, neural network classifiers, bootstrap aggregated trees, and the like.

Figure 4:
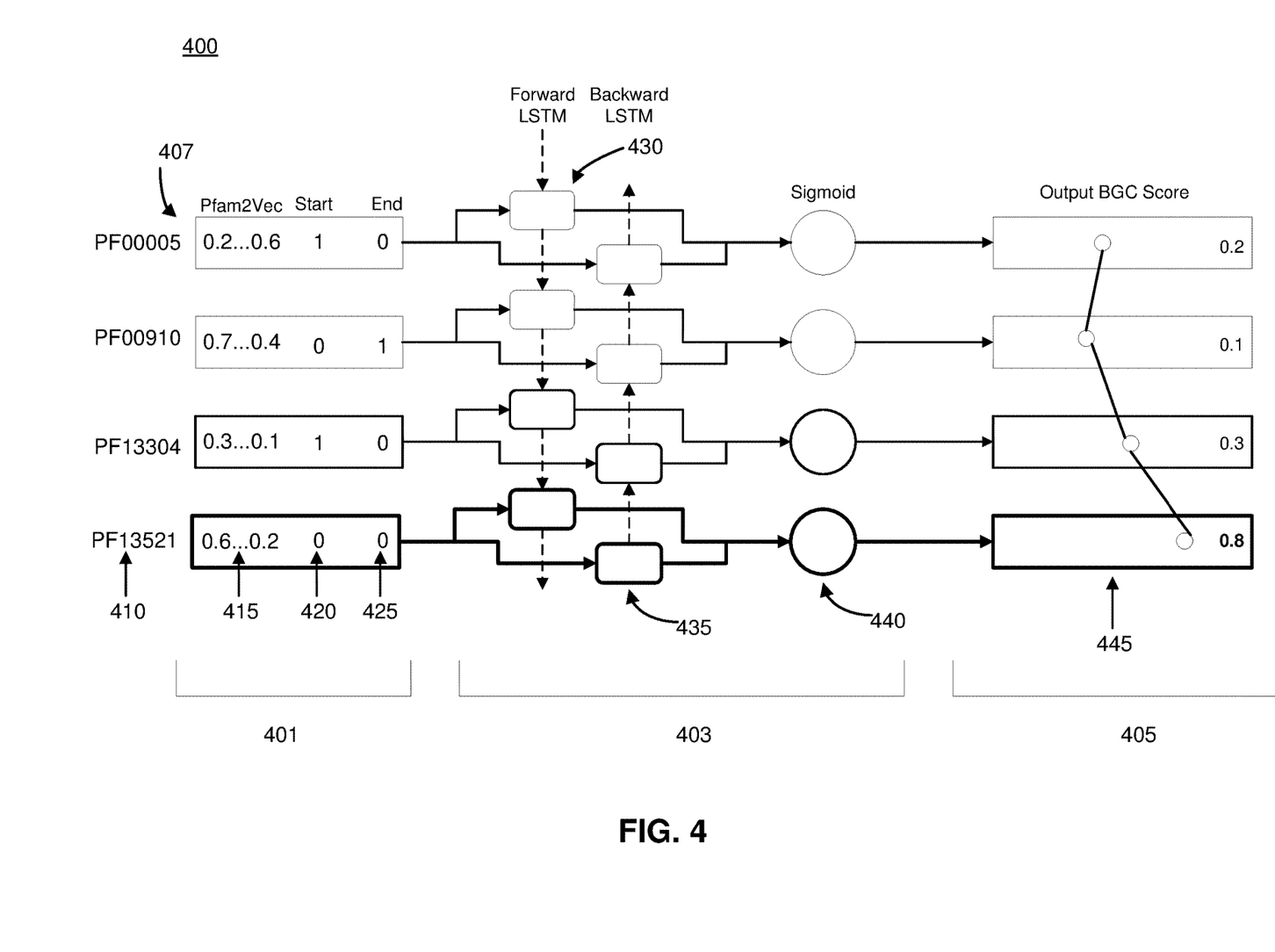
FIG. 4 illustrates a neural network for obtaining BGC classification scores for domains in a genome, according to one embodiment.

FIG. 4 illustrates the process of obtaining BGC classification scores for pfam domains in a genome sequence, according to one embodiment. In the embodiment shown, a BiLSTM neural network 400 is used to obtain the BGC classification scores. The BiLSTM neural network 400 is comprised of three layers: an input layer 401, a BiLSTM layer 403, and an output layer 405. Each row in FIG. 4 represents a timestep where the BiLSTM neural network 400 processes a pfam domain from the input sequence maintained in genomic order. For example, the last timestep shown corresponds to the processing of pfam domain PF13521 410.

The input layer 401 encodes a sequence of numerical vectors representing pfam domains identified from the genome sequences using a shallow neural network. To obtain the sequence of numerical vectors, the pfam2vec model may be employed. The pfam2vec model is generated from a modified version of the word2vec skip-gram algorithm. In the pfam2vec model, genomes are viewed as text documents, BGC regions as paragraphs, and pfam domain identifiers as words. In doing so, natural language processing techniques are used to identify contextual similarities between pfam domains and BGC regions based on the ordered sequences of pfam domain identifiers. For each domain, the pfam2vec embedding outputs a vector of real numbers that encapsulates the domain properties based on its genomic context, from which contextual and functional similarities between pfam domains and BGCs is leveraged.

A vector consisting of one or more binary flags is also computed for each pfam domain. The binary flags indicate where in the protein the pfam domain is located. In some embodiments, one binary flag, e.g., binary flag 420, indicates if the pfam domain is found at the start of the protein, and a second binary flag, e.g., 425, indicates if the pfam domain is found at the end of the protein. In this example, pfam domain PF13521 410 is neither at the start nor end of the protein, shown as "0" in the binary flags 420 and 425. In other embodiments, one or more different binary flags can indicate the pfam domain's relative position within the protein or genome. The numerical vector, e.g., numerical vector 415, and binary flag vector are concatenated into a single input vector to produce the input layer, e.g., input 407, that will be fed into the BiLSTM layer 403.

Training and validating of the pfam2vec model is performed to select parameters, including the number of dimensions in the vector (e.g., 50, 100, 200), the number of training iterations, and the type of architecture (e.g., skip-gram, continuous bag of words (CBOW), etc.). A corpus of documents and words is used to train the pfam2vec model. Each document may consist of a space-separated list of pfam domain identifiers that represent all pfam domains within a genome, maintained in their genomic order. To evaluate the pfam2vec embedding, cosine similarity of domain vectors is used in comparison with domain membership to pfam superfamilies (clans) from a genome database (e.g., Pfam database version 31). The cosine similarity of all (non-identity) pairs of domains from all pfam superfamilies is compared to cosine similarity of all pairs from pfam superfamilies that were randomly shuffled. The average pfam2vec vector representation of each BGC from the MIBiG set is calculated as an average of its list of pfam2vec vectors, with averages computed separately for each dimension.

In one embodiment, the BiLSTM layer 403 consists of forward and backward LSTM network layers, each consisting of a basic LSTM unit (i.e., a memory cell) with a 128-dimensional hidden state vector. LSTM units, e.g., 430 and 435, are units of RNN that propagate information from earlier time steps to aid in analysis at later timesteps. LSTM units enable recurrent nets to continue learning through additional timesteps and processing layers. Each memory cell is fed a single input vector (full arrows) as well as the cell's state from the previous time step in the genome (dashed arrows). The backward LSTM layer processes the vectors in reverse order, making the BiLSTM layer 403 bi-directional.

At each time step, the output of the BiLSTM layer 403 is passed to the output layer 405 through a single fully-connected node. The output layer 405 may be a time-distributed Dense layer with a sigmoid activation function, e.g., sigmoid activation function 440. In other embodiments, different activation functions can be used to calculate the prediction score, namely, linear functions, ReLu functions, tanh functions, etc. The activation function produces a single output unit for each timestep, e.g., input 407. The output unit for each timestep is a BGC classification score between zero and unity that represents the likelihood that the corresponding pfam domain is a part of a BGC gene. For example, the output for pfam domain PF13521 410 is 0.8 which is represented in the output layer 405 at output 445. In some embodiments, more than one BGC classification score is used to describe the BGC classification confidence of each pfam domain. Examples include scores for upper and lower confidence limits, median confidence scores, standard deviation of the confidence scores, and the like.

In one embodiment, BGC predictions are averaged across each gene, and candidate BGC genes are selected using a pre-determined threshold. Consecutive BGC genes are merged into putative BGCs. Optionally, postprocessed BGC regions are created by applying filters. For example, BGC regions at most one gene apart can be merged, BGC regions containing less than a threshold number of nucleotides (e.g., 1000, 2000, 5000) may be filtered out, and BGC regions with no known biosynthetic domains may also be filtered out. Known biosynthetic domains may be from a list published in a genome database, e.g., National Center for Biotechnology Information (NCBI), antiSMASH, etc.

RNN Model Training

Figure 5:
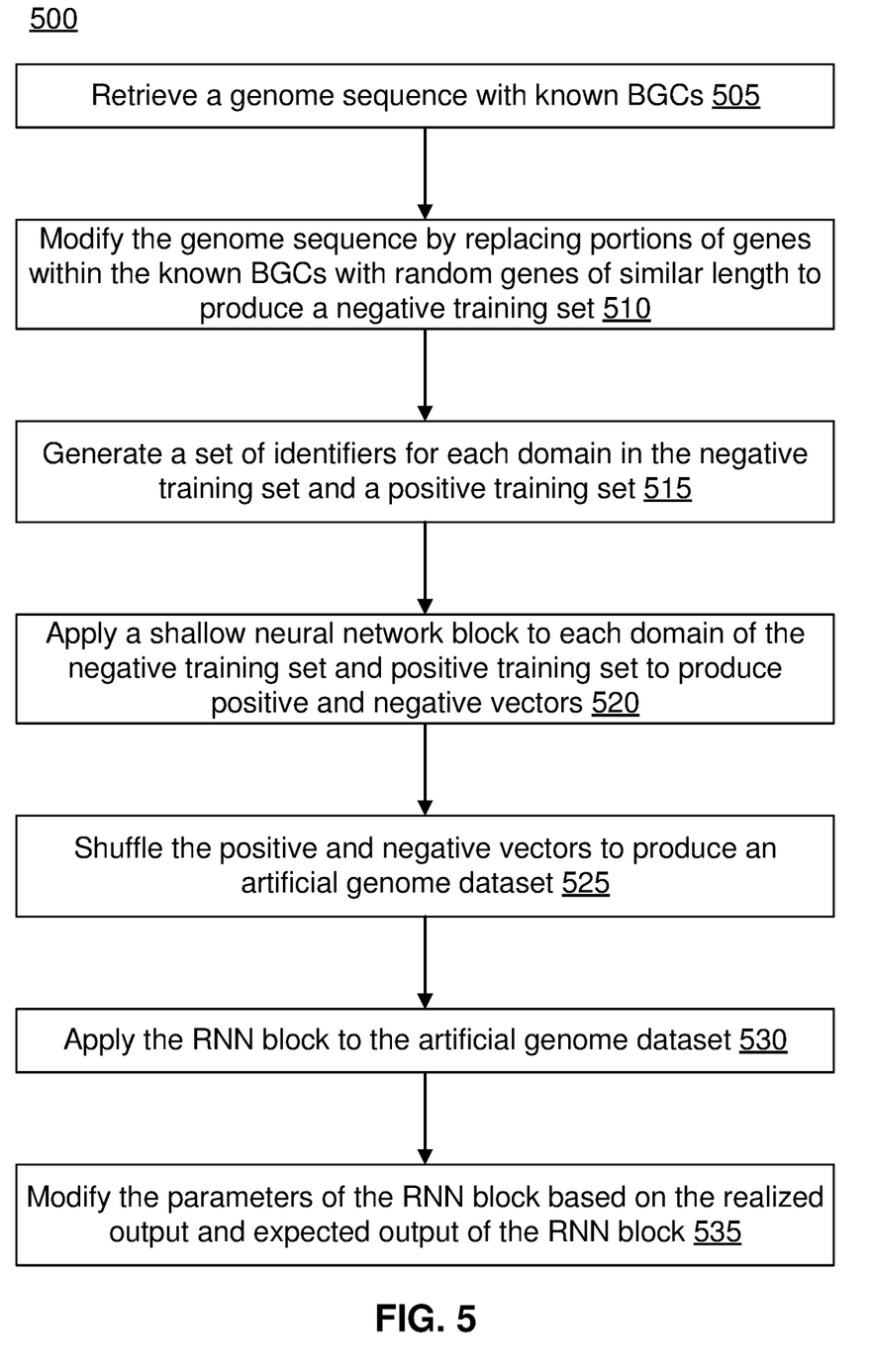
FIG. 5 illustrates a method for training a recurrent neural network using positive and negative training sets, according to one embodiment.

FIG. 5 illustrates a method 500 for training a recurrent neural network using positive and negative training sets, according to one embodiment. A positive training set may be collected by obtaining BGC labeled sequences from a genome database. Additional data such as the location of the known BGCs, the biosynthetic product, and/or chemical activity of the known BGCs can also be collected from third-party databases or using genome processing software. In other embodiments, BGCs are labeled by the BGC prediction system 115.

To generate a negative training set, a genome sequence with known BGCs is retrieved 505. The genome sequence is modified 510 by identifying the location of the known BGCs within the genome and replacing portions of the BGCs' genes with random genes of similar lengths from reference sequences. This greatly reduces the likelihood that the BGC genes will produce secondary metabolites and creates genomes unlikely to contain any BGCs. To do this, a reference set of sequences is collected and preprocessed. Examples of reference sets include sequences published on public databases, sequences published by the National Center for Biotechnology Information (NCBI), and the like. Reference sequences may be of bacterial genomes, or other genome types, e.g., viral genomes, prokaryotic genomes, eukaryotic genomes, etc. For each reference sequence, regions similar to known BGC are removed. For example, regions similar to known MIBiG BGC may be removed from reference bacteria with a pre-determined level of confidence (e.g., 95%). To generate a single negative sample, a random reference sequence and a random sample from genome sequence with know BGCs are selected. Each BGC gene in the genome sequence with known BGCs is replaced with a random gene from the reference sequence, while considering only a percentage of genes that were most similar in number of Pfam domains (e.g., 1%, 2%, 5%, etc.). Multiple samples may be generated from each reference sequence to produce the negative training set.

A set of identifiers is generated 515 for each domain in each sequence of the negative and positive training sets. The positive and negative training sets are converted into their respective pfam2vec vectors by applying 520 the pfam2vec model to the sets of identifiers to produce positive and negative vectors. Positive and negative BGC vectors are repeatedly shuffled and concatenated 525 to generate artificial genome datasets that simulate the real genomic context in which BGCs are scattered randomly throughout the genome and surrounded by non-BGC sequences.

A RNN block is applied 530 to the artificial genome datasets to produce a BGC classification score for each domain. The parameters of the RNN block are modified 535 based on the realized output of the RNN block and the expected output of the RNN block. The RNN block may be applied 530 and modified 535 iteratively until one or more training criteria are met (e.g., a predetermined number of iterations, an accuracy metric of the RNN block exceeding a training threshold, etc.). For example, a bootstrap sampling technique may be employed for optimizing model architecture, input features, and parameters. Bootstrapping may be performed using the artificially generated genome datasets, and in each iteration, a fraction of the annotated genomes is randomly selected for validation and the remainder for testing. An averaged Receiver Operating Characteristic (ROC) curve is obtained by combining the predictions from each iteration test set. Final parameter configuration of the model is chosen based on the highest test area under the curve (AUC) across all tested configurations.

Figure 6:
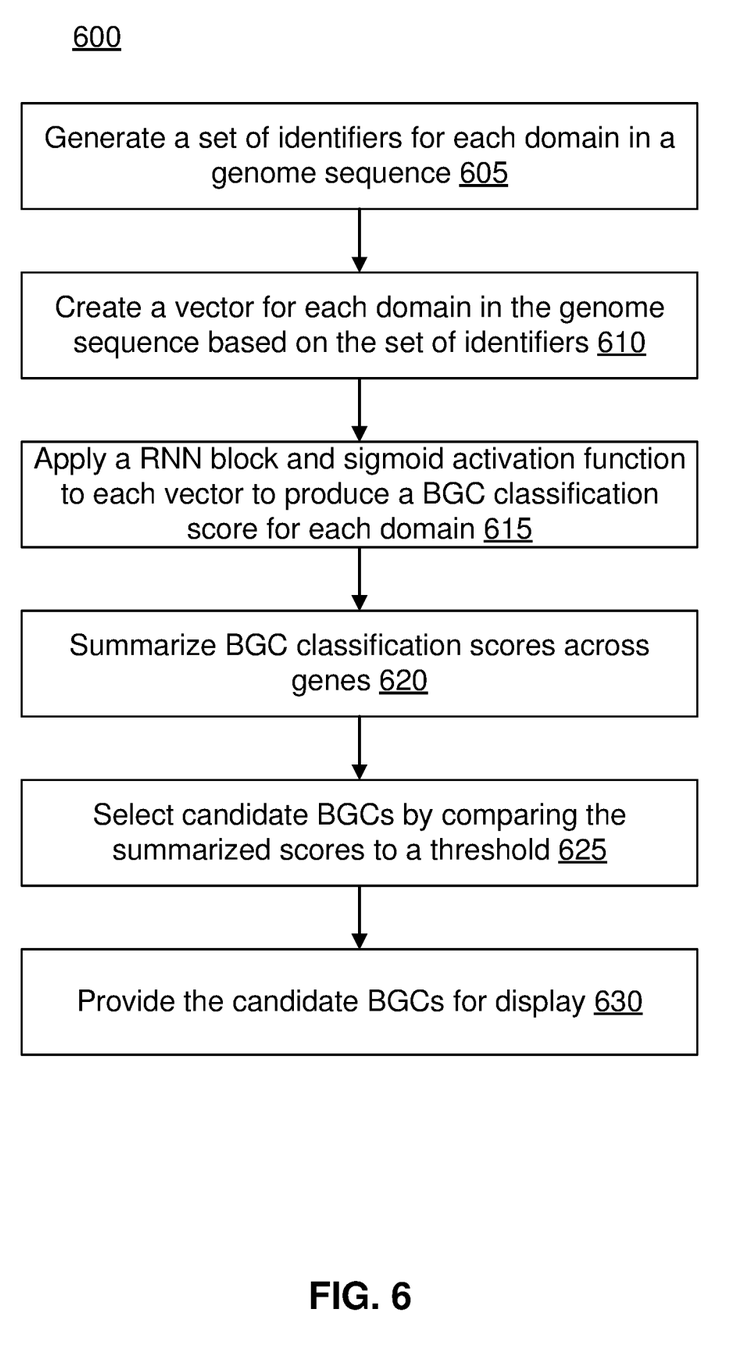
FIG. 6 illustrates a method for identifying candidate BGCs within a genome, according to one embodiment.

FIG. 6 illustrates a method 600 for identifying candidate BGCs within a genome, according to one embodiment. A set of identifiers are identified 605 for each domain in a genome sequence. A vector for each domain in the genome sequence is created 610 based on the set of identifiers. A RNN and sigmoid activation function are applied 615 to each vector to produce a BGC classification score for each domain. BGC classification scores are summarized 620 across genes to produce a single classification score for each gene. Candidate BGCs are selected 625 by comparing the summarized classifications scores to a threshold. Candidate BGCs are provided 630 for display to a user.

What is claimed is:

1. A method comprising:
   identifying, in a genome sequence, a set of domains, each identified domain corresponding to a set of domain identifiers;
   applying a shallow neural network block to each set of domain identifiers to produce a set of vectors, each vector corresponding to a set of domain identifiers;
   applying a recurrent neural network (RNN) block to the set of vectors to produce a biosynthetic gene cluster (BGC) class score for each domain, wherein the RNN block was trained by:
   identifying a set of positive vectors representing known BGCs;
   synthesizing a set of negative vectors unlikely to represent BGCs;
   applying the RNN block to the positive and negative sets of vectors to generate predictions of whether each vector is a positive or negative vector; and
   updating weights of the RNN block based on the predictions;
   selecting candidate BGCs by averaging BGC class scores across genes within a domain and comparing the average BGC class scores to a threshold;
   predicting a molecular activity of biosynthetic products derived from the selected BGCs; and
   providing for display, on a user interface, the candidate BGCs and predicted molecular activity.

2. The method of claim 1, further comprising:
   processing candidate BGCs, wherein processing includes merging and filtering candidate BGCs based on at least one of: a presence of known BGCs, a cluster length, or a distance between candidate BGCs.

3. The method of claim 1, further comprising:
   merging consecutive candidate BGC genes that are adjacent in the genome sequence.

4. The method of claim 1, wherein the RNN block is a bi-directional long short-term memory (LSTM) block.

5. The method of claim 1, wherein the domain identifiers are maintained in genomic order.

6. The method of claim 1, wherein each vector in the set of vectors comprises one hundred elements, each element being a real number, each element representing a property of the domain based on its genomic context.

7. The method of claim 1, further comprising:
   predicting, for each candidate BGC, with a classifier, a secondary metabolite class based on a biosynthetic product and molecular activity of the candidate BGC.

8. The method of claim 7, wherein the classifier is a random forest classifier.

9. The method of claim 1, wherein the set of negative vectors are synthesized by:

retrieving a genome sequence with known BGCs;
modifying the genome sequence by replacing a portion of the genes within the known BGCs with random genes of similar length;
generating a set of identifiers for each domain in the modified genome sequence; and
applying a shallow neural network block to each domain in the modified genome sequence to produce a negative set of vectors.

10. The method of claim 1, wherein applying the RNN block to the set of vectors further comprises applying a sigmoid activation function.

11. A non-transitory computer-readable storage medium containing computer program code comprising instructions that, when executed by a processor, causes the processor to:
identify, in a genome sequence, a set of domains, each identified domain corresponding to a set of domain identifiers;
apply a shallow neural network block to each set of domain identifiers to produce a set of vectors, each vector corresponding to a set of domain identifiers;
apply a recurrent neural network (RNN) block to the set of vectors to produce a biosynthetic gene cluster (BGC) class score for each domain, wherein the RNN block was trained by:
identifying a set of positive vectors representing known BGCs;
synthesizing a set of negative vectors unlikely to represent BGCs;
applying the RNN block to the positive and negative sets of vectors to generate predictions of whether each vector is a positive or negative vector; and
updating weights of the RNN block based on the predictions;
select candidate BGCs by averaging BGC class scores across genes within a domain and comparing the average BGC class scores to a threshold;
predict a molecular activity of biosynthetic products derived from the selected BGCs; and
provide for display, on a user interface, the candidate BGCs and predicted molecular activity.

12. The non-transitory computer-readable storage medium of claim 11, wherein the instructions, when executed by the processor, further cause the processor to:
process candidate BGCs by merging and filtering candidate BGCs based on at least one of: a presence of known BGCs, a cluster length, or a distance between candidate BGCs.

13. The non-transitory computer-readable storage medium of claim 11, wherein the instructions, when executed by the processor, cause the processor to:
merge consecutive candidate BGC genes.

14. The non-transitory computer-readable storage medium of claim 11, wherein the RNN block is a bi-directional long short-term memory (LSTM) block.

15. The non-transitory computer-readable storage medium of claim 11, wherein the domain identifiers are maintained in genomic order.

16. The non-transitory computer-readable storage medium of claim 11, wherein each vector in the set of vectors comprises one hundred elements, each element being a real number, each element representing a property of the domain based on its genomic context.

17. The non-transitory computer-readable storage medium of claim 11, wherein the instructions, when executed by the processor, further cause the processor to:
predict, for each candidate BGC, with a classifier, a secondary metabolite class based on a biosynthetic product and molecular activity of the candidate BGC.

18. The non-transitory computer-readable storage medium of claim 17, wherein the classifier is a random forest classifier.

19. The non-transitory computer-readable storage medium of claim 17, wherein the set of negative vectors are synthesized by:
retrieving a genome sequence with known BGCs;
modifying the genome sequence by replacing a portion of the genes within the known BGCs with random genes of similar length;
generating a set of identifiers for each domain in the modified genome sequence; and
applying a shallow neural network block to each domain in the modified genome sequence to produce a negative set of vectors.

20. The non-transitory computer-readable storage medium of claim 11, wherein the instructions that cause the processor to apply the RNN block to the set of vectors further comprise instructions that cause the processor to apply a sigmoid activation function.

* * * * *